United States Patent
Halla et al.

(10) Patent No.: US 7,399,274 B1
(45) Date of Patent: *Jul. 15, 2008

(54) SENSOR CONFIGURATION FOR A CAPSULE ENDOSCOPE

(75) Inventors: Brian Lester Halla, Saratoga, CA (US); Joseph Domenick Montalbo, Menlo Park, CA (US); Gobi R. Padmanabhan, Sunnyvale, CA (US); Peter Yi-Ning Wang, Fremont, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 302 days.

This patent is subject to a terminal disclaimer.

(21) Appl. No.: 10/643,457

(22) Filed: Aug. 19, 2003

(51) Int. Cl.
*A61B 1/04* (2006.01)
(52) U.S. Cl. .................. 600/160; 600/109; 600/476
(58) Field of Classification Search .......... 600/160, 600/109, 407, 476, 473, 474, 549, 547, 561; 348/65, 76
See application file for complete search history.

(56) References Cited

U.S. PATENT DOCUMENTS

| | | | |
|---|---|---|---|
| 3,456,134 A | 7/1969 | Ko | |
| 4,177,800 A | 12/1979 | Enger | |
| 4,435,050 A | 3/1984 | Poler | |
| 4,467,361 A * | 8/1984 | Ohno et al. | 348/340 |
| 4,508,766 A * | 4/1985 | Inaike et al. | 427/99.4 |
| 4,585,456 A | 4/1986 | Blackmore | |
| 4,928,172 A | 5/1990 | Uehara et al. | |
| 5,177,670 A * | 1/1993 | Shinohara et al. | 361/738 |
| 5,258,025 A | 11/1993 | Fedorov et al. | |
| 5,318,557 A | 6/1994 | Gross | |
| 5,510,273 A * | 4/1996 | Quinn | 156/160 |
| 5,603,328 A | 2/1997 | Zucker et al. | |
| 5,604,531 A | 2/1997 | Iddan et al. | |
| 5,876,339 A | 3/1999 | Lemire | |
| 5,965,875 A | 10/1999 | Merrill | |
| 6,025,873 A | 2/2000 | Nishioka et al. | |
| 6,049,094 A * | 4/2000 | Penry | 257/99 |

(Continued)

FOREIGN PATENT DOCUMENTS

JP 4-180736 * 6/1992

(Continued)

OTHER PUBLICATIONS

Lin, Gisela et al., May 20, 2004, "Improved Sensor Pills for Physiological Monitoring," pp. 1-2. Can be found at http://www.nasatech.com/Briefs/Feb00/NP020652.html.

(Continued)

*Primary Examiner*—John P. Leubecker
(74) *Attorney, Agent, or Firm*—Darby & Darby PC; John W. Branch

(57) ABSTRACT

The present invention provides a capsule endoscope (CE) having sensors configured to form or to conform to the shell of the CE. The sensors are curved to correspond to the capsule's shape. According to this embodiment, the sensors may be covered by a coating material to protect the sensors. The sensors may also form the capsule shell. Instead of being covered by a shell associated with the capsule, the sensors are formed as the capsule shell. The sensors may also form part of the capsule shell. For example, one half of the capsule shell may be formed from the sensors.

20 Claims, 7 Drawing Sheets

U.S. PATENT DOCUMENTS

| | | | |
|---|---|---|---|
| 6,051,877 A * | 4/2000 | Usami et al. | 257/679 |
| 6,057,909 A | 5/2000 | Yahav et al. | |
| 6,165,813 A * | 12/2000 | Quinn et al. | 438/67 |
| 6,169,318 B1 * | 1/2001 | McGrath | 257/445 |
| 6,192,267 B1 | 2/2001 | Scherninski et al. | |
| 6,240,312 B1 | 5/2001 | Alfano et al. | |
| 6,261,226 B1 * | 7/2001 | McKenna et al. | 600/109 |
| 6,285,400 B1 * | 9/2001 | Hokari | 348/374 |
| 6,300,612 B1 * | 10/2001 | Yu | 250/208.1 |
| 6,348,411 B1 * | 2/2002 | Ireland et al. | 438/672 |
| 6,392,143 B1 * | 5/2002 | Koshio | 174/528 |
| 6,425,858 B1 | 7/2002 | Minami | |
| 6,428,469 B1 | 8/2002 | Iddan et al. | |
| 6,632,175 B1 | 10/2003 | Marshall | |
| 6,638,304 B2 | 10/2003 | Azar | |
| 6,709,387 B1 | 3/2004 | Glukhovsky et al. | |
| 6,749,633 B1 | 6/2004 | Lorenzo et al. | |
| 6,752,888 B2 * | 6/2004 | Hosier et al. | 156/160 |
| 6,764,440 B2 | 7/2004 | Iddan et al. | |
| 6,771,007 B2 | 8/2004 | Tanielian | |
| 6,791,072 B1 * | 9/2004 | Prabhu | 250/208.1 |
| 6,828,908 B2 | 12/2004 | Clark | |
| 6,830,135 B2 | 12/2004 | Lin et al. | |
| 6,839,135 B2 * | 1/2005 | Hamm et al. | 356/328 |
| 6,881,943 B1 * | 4/2005 | Yegnashankaran | 250/208.1 |
| 6,885,818 B2 | 4/2005 | Goldstein | |
| 6,895,270 B2 | 5/2005 | Ostrovsky | |
| 6,904,308 B2 | 6/2005 | Frisch et al. | |
| 7,041,493 B2 | 5/2006 | Rao | |
| 7,044,908 B1 | 5/2006 | Montalbo et al. | |
| 2001/0020671 A1 * | 9/2001 | Ansorge et al. | 250/208.1 |
| 2001/0035902 A1 | 11/2001 | Iddan et al. | |
| 2001/0051766 A1 | 12/2001 | Gazdzinski | |
| 2002/0032366 A1 | 3/2002 | Iddan et al. | |
| 2002/0042562 A1 | 4/2002 | Meron et al. | |
| 2002/0089595 A1 | 7/2002 | Orava et al. | |
| 2002/0103417 A1 | 8/2002 | Gazdziniski | |
| 2002/0103439 A1 | 8/2002 | Zeng et al. | |
| 2002/0107444 A1 | 8/2002 | Adler | |
| 2002/0109774 A1 * | 8/2002 | Meron et al. | 348/74 |
| 2002/0123325 A1 | 9/2002 | Cooper | |
| 2002/0173700 A1 | 11/2002 | Kim et al. | |
| 2002/0198470 A1 | 12/2002 | Imran et al. | |
| 2003/0020810 A1 | 1/2003 | Takizawa et al. | |
| 2003/0060683 A1 | 3/2003 | Abe et al. | |
| 2003/0117491 A1 | 6/2003 | Avini et al. | |
| 2003/0130562 A1 * | 7/2003 | Barbato et al. | 600/109 |
| 2003/0171653 A1 * | 9/2003 | Yokoi et al. | 600/160 |
| 2003/0195415 A1 * | 10/2003 | Iddan | 600/424 |
| 2003/0222223 A1 | 12/2003 | Kamei et al. | |
| 2004/0027459 A1 * | 2/2004 | Segawa et al. | 348/207.99 |
| 2004/0032187 A1 * | 2/2004 | Penner et al. | 310/311 |
| 2004/0044393 A1 | 3/2004 | Yarden et al. | |
| 2004/0054278 A1 * | 3/2004 | Kimchy et al. | 600/407 |
| 2004/0073267 A1 | 4/2004 | Holzer | |
| 2004/0087832 A1 | 5/2004 | Glukhovsky et al. | |
| 2004/0092825 A1 | 5/2004 | Madar et al. | |
| 2004/0092828 A1 | 5/2004 | Hoppe et al. | |
| 2004/0106849 A1 | 6/2004 | Cho et al. | |
| 2004/0111011 A1 | 6/2004 | Uchiyama et al. | |
| 2004/0249245 A1 * | 12/2004 | Irion | 600/160 |
| 2004/0254455 A1 * | 12/2004 | Iddan | 600/424 |
| 2006/0185165 A1 * | 8/2006 | Vafi et al. | 29/854 |

FOREIGN PATENT DOCUMENTS

| | | | |
|---|---|---|---|
| WO | WO-94/23334 | | 10/1994 |
| WO | WO-01-53792 | * | 7/2001 |

OTHER PUBLICATIONS

Lin, Gisela and William Tang, May 20, 2004, "Wearable Sensor Patches for Physiological Monitoring," pp. 1-2. Can be found at http://www.nasatech.com/Briefs/Feb00/NP020651.html.

Astaras, Alexander et al., Dec. 4-7, 2002, "A Miniature Integrated Electronics Sensor Capsule for Real-Time Monitoring of the Gastrointestinal Tract (IDEAS)." ICBME 2002: "The Bio-Era: New Challenges, New Frontiers."

U.S. Appl. No. 10/281,836, filed Oct. 28, 2002, Mohan Yegnashankaran.

U.S. Appl. No. 10/641,625 Final Rejection Jul. 18, 2007; Non-final Rejection Jan. 24, 2007; Final Rejection Oct. 19, 2006; Non-final Rejection Feb. 6, 2006; Final Rejection Jul. 28, 2005; Non-final Rejection Jun. 9, 2005.

U.S. Appl. No. 10/615,759 Advisory Action Mar. 26, 2007; Final Rejection Feb. 12, 2007; Non-final Rejection Jul. 31, 2006; Advisory Action Jun. 8, 2006; Advisory Action May 4, 2006; Final rejection Mar. 27, 2006; Non-final Rejection Oct. 24, 2005; Non-final Rejection Jun. 20, 2005.

U.S. Appl. No. 10/643,652 Final Rejection Jun. 15, 2007; Advisory Action Mar. 12, 2007; Final Rejection Feb. 12, 2007; Advisory Action Nov. 1, 2006; Final Rejection Sep. 13, 2006; Non-final Rejection Mar. 22, 2006.

U.S. Appl. No. 10/646,636 Final Rejection Jul. 17, 2007; Advisory Action Mar. 7, 2007; Final Rejection Jan. 22, 2007; Non-final Rejection Aug. 3, 2006; Advisory Action Jun. 8, 2006; Final Rejection Feb. 27, 2006.

U.S. Appl. No. 10/642,415 Non-final Rejection Aug. 22, 2005; Non-final Rejection Mar. 8, 2007; Non-final Rejection Sep. 14, 2006.

U.S. Appl. No. 10/616,387 Non-final Rejection May 4, 2007; Non-final Rejection Oct. 4, 2006; Final Rejection Jun. 27, 2006; Non-final Rejection Dec. 20, 2005; Advisory Action Sep. 16, 2005; Final Rejection Jun. 28, 2005; Non-final Rejection Feb. 7, 2005.

U.S. Appl. No. 10/615,761 Non-final Rejection Sep. 2, 2005; Notice of Allowance Feb. 17, 2006.

U.S. Appl. No. 10/616,040 Non-final Rejection Jun. 20, 2005; Final Rejection Oct. 14, 2005; Advisory Action Dec. 20, 2005; Non-final Rejection Jun. 1, 2006; Non-final Rejection Oct. 18, 2006; Final Rejection Apr. 10, 2007; Advisory Action Jun. 20, 2007.

U.S. Appl. No. 10/642,415 Final Rejection Oct. 31, 2007.

U.S. Appl. No. 10/616,387 Final Rejection Oct. 18, 2007.

U.S. Appl. No. 10/616,040 Non-final No. 29, 2007.

U.S. Appl. No. 10/616,040 Application and Figures Jul. 8, 2003.

U.S. Appl. No. 11/761,975 Application and Figures Jun. 12, 2007.

U.S. Appl. No. 10/641,625 Application and Figures Aug. 15, 2003.

U.S. Appl. No. 10/643,652 Application and Figures Aug. 19, 2003.

U.S. Appl. No. 10/646,636 Application and Figures Aug. 21, 2003.

U.S. Appl. No. 10/642,415 Application and Figures Aug. 15, 2003.

U.S. Appl. No. 10/616,387 Application and Figures Jul. 8, 2003.

U.S. Appl. No. 10/616,040 Application and Figures Jul. 8, 2003.

U.S. Appl. No. 10/616,040 Application and Figures Feb. 18, 2003.

* cited by examiner

US 7,399,274 B1

SENSOR CONFIGURATION FOR A CAPSULE ENDOSCOPE

FIELD OF THE INVENTION

The present invention is related to electronic sensors for capsule endoscopes, and more specifically to sensor configuration for capsule endoscopes.

BACKGROUND OF THE INVENTION

Endoscope inspection is a tool commonly used in detecting gastro-intestinal (GI) diseases. As the endoscope proceeds through the GI tract sensor readings may be obtained to detect the abnormalities.

The endoscope inspection may utilize many different sensors to observe and detect abnormalities within the GI tract. These sensors may include imaging sensors, temperature sensors, pH sensors, as well as other types of sensors.

One such endoscope tool is a capsule that is swallowed by the patient. For many of the patients the capsule moves through the GI tract within a twenty-four hour period. An advantage of the endoscope capsule is that during the GI inspection the patient is generally not hooked up to external machinery. There are many disadvantages; however, that are associated with the capsule.

One disadvantage is that it is difficult to configure the sensors for the capsule. As the capsule size is small, space is at a premium making the configuration of the sensors important. What is needed, therefore, is a way to more efficiently configure the sensors associated with the capsule.

SUMMARY OF THE INVENTION

Briefly described, the present invention is directed at providing sensors configured to form or to conform to the capsule shell.

According to one aspect of the invention, sensors are formed to correspond to the capsule's shape. According to this embodiment, the sensors are covered by the shell of the capsule.

According to another aspect of the invention, the sensors form the capsule shell. Instead of being covered by a shell associated with the capsule, the sensors are formed as the capsule shell itself.

According to yet another aspect of the invention, the sensors form part of the capsule shell. For example, one half of the capsule shell may be formed from the sensors.

DETAILED DESCRIPTION OF THE PREFERRED EMBODIMENT

Figure 1:
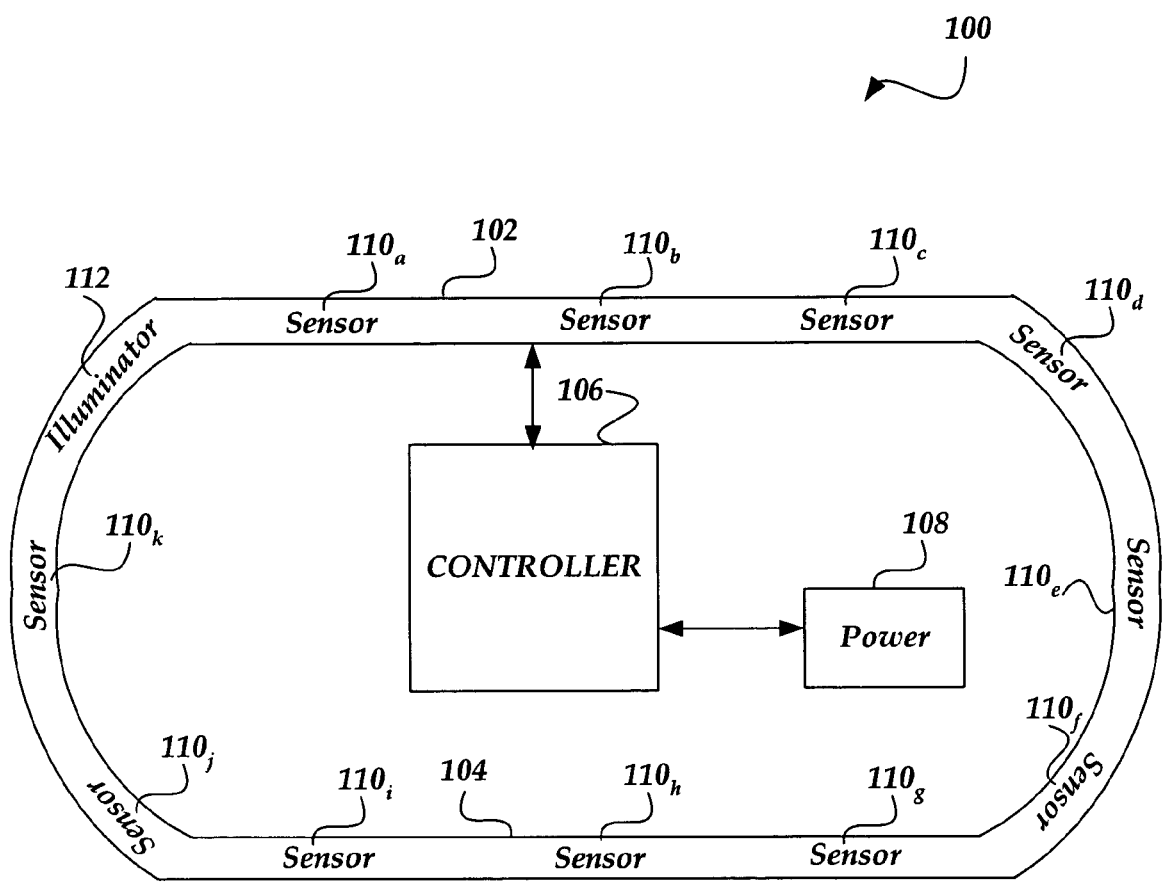
FIG. 1 shows a schematic diagram of a capsule endoscope wherein the shell contains an exemplary sensor configuration.

In the following detailed description of exemplary embodiments of the invention, reference is made to the accompanied drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated herein, unless the context clearly dictates otherwise. The meaning of "a," "an," and "the" includes plural reference, the meaning of "in" includes "in" and "on." The term "connected" means a direct electrical connection between the items connected, without any intermediate devices. The term "coupled" means either a direct electrical connection between the items connected or an indirect connection through one or more passive or active intermediary devices. The term "circuit" means either a single component or a multiplicity of components, either active and/or passive, that are coupled together to provide a desired function. The term "signal" means at least one current, voltage, or data signal. Referring to the drawings, like numbers indicate like parts throughout the views.

The terms "comprising," "including," "containing," "having," and "characterized by," mean an open-ended or inclusive transitional construct and does not exclude additional, unrecited elements, or method steps. For example, a combination that comprises A and B elements, also reads on a combination of A, B, and C elements.

The term "endoscope" means a small, flexible tube with a light and a lens on the end. It can be used to look into the gastrointestinal (GI) tract of a patient, e.g., the esophagus, stomach, duodenum, colon, or rectum. It can also be employed to take tissue from the GI tract for testing, to provide therapeutic drugs to a particular location in the GI tract, and to take color photographs of the inside of the body. There are many types of endoscopes, including, but not limited to, colonoscopes and sigmoidoscopes.

The term capsule endoscope (CE) means a "capsule" or "pill" shaped diagnostic device for observing characteristics in the lining of the GI tract of a patient although various shapes may be employed. The CE is orally administered and may be propelled by peristalsis to move throughout the entire length of the gastrointestinal tract where it is eventually excreted by the patient. In one embodiment, the capsule endoscope can produce images of the internal lining of the GI tract either along its entire length or at sections of particular interest to medical professionals. The images may be stored in the capsule endoscope or broadcast to a receiver outside the body. The images may be illuminated by various wavelengths of light (both visible and non-visible as well as other forms of electromagnetic radiation such as X-rays) by sources included in the capsule endoscope.

Other embodiments of the capsule endoscope may be arranged to measure temperature, pH level, or any other characteristic of the GI tract. Some embodiments of the capsule endoscope may be arranged to enable an operator to control the movement of the capsule endoscope along the GI tract, other embodiments may be configured to enable the capsule endoscope to take a biopsy of the lining of the GI tract, and still other embodiments may be arranged to enable the capsule endoscope to provide a therapeutic treatment to a particular location in the GI tract.

Additionally, although a CE is not intended to be limited to the particular "shape" or size of a capsule, one embodiment of the capsule endoscope could have an elongated "capsule" shape with dimensions of approximately 11 millimeters by 26 millimeters.

The invention is directed to providing a sensor configuration for a CE that is employed to observe characteristics in the lining of the gastrointestinal tract of a patient. As mentioned elsewhere, these characteristics can be images, temperature, pH level and the like. The inventive CE is arranged such that the sensors are formed as part of the capsule shell, or formed to follow the contours of the shell.

FIG. 1 shows a schematic diagram of a capsule endoscope wherein the shell is formed from an exemplary sensor configuration, in accordance with aspects of the invention. Exemplary capsule endoscope (CE) 100 is "capsule" shaped and sized for oral administration to a patient. Several components are disposed inside CE 100 including controller 106, which is coupled to power 108. Controller 106 is configured to control operation of the sensors and other devices that may be contained within the CE. Sensors $110_{a-l}$ are disposed in the outer surface of CE 100 and form the shell of CE 100. Illuminator 112 is positioned on the shell. Illuminator 112 provides light for illuminating the lining of a patient's gastrointestinal tract and sensors $110_{a-l}$ are configured to collect data. For example, at least one of the sensors may be an imager to capture images of the illuminated lining. Additionally, an illuminator may provide light of a selected wavelength that is most suited to observing a particular characteristic of the lining of the patient's gastrointestinal tract. Other sensors may be configured to measure pH level, temperature, and the like.

An outer shell coating may be disposed over the other sensors to provide protection to CE 100 (not shown). Also, at least a portion of the outer surface of CE 100 may be coated with a medicine to prevent clotting such as heparin, and the like. The outer surface of CE 100 may be manufactured or coated from materials that are known to be biologically inert, such as plastic, nylon, composite, stainless steel, and the like.

Figure 8:
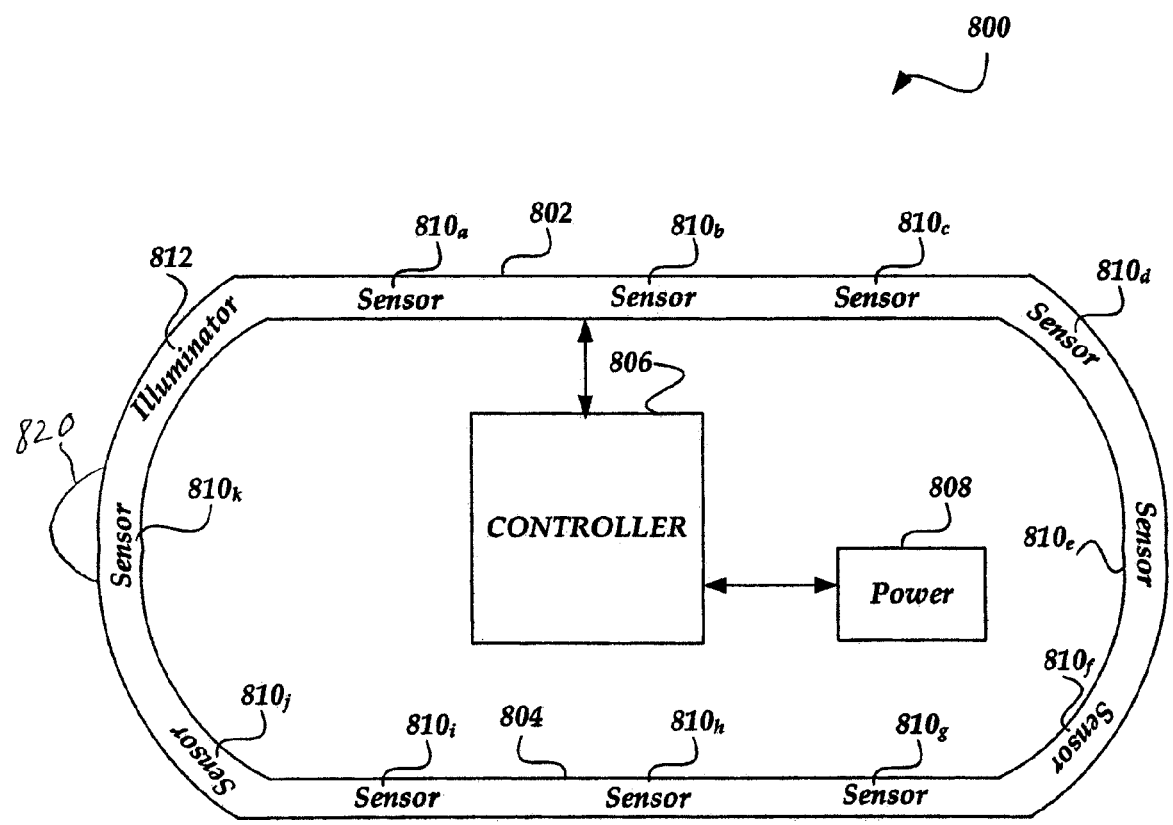
FIG. 8 shows a schematic diagram of an embodiment of the capsule endoscope of FIG. 1.

In another embodiment (not shown), a lens and/or a filter may enable a sensor (110) to capture different resolutions and/or aspects of images of the lining of a patient's gastrointestinal tract. FIG. 8 shows an embodiment of a capsule endoscope with lens 820.

Figure 2:
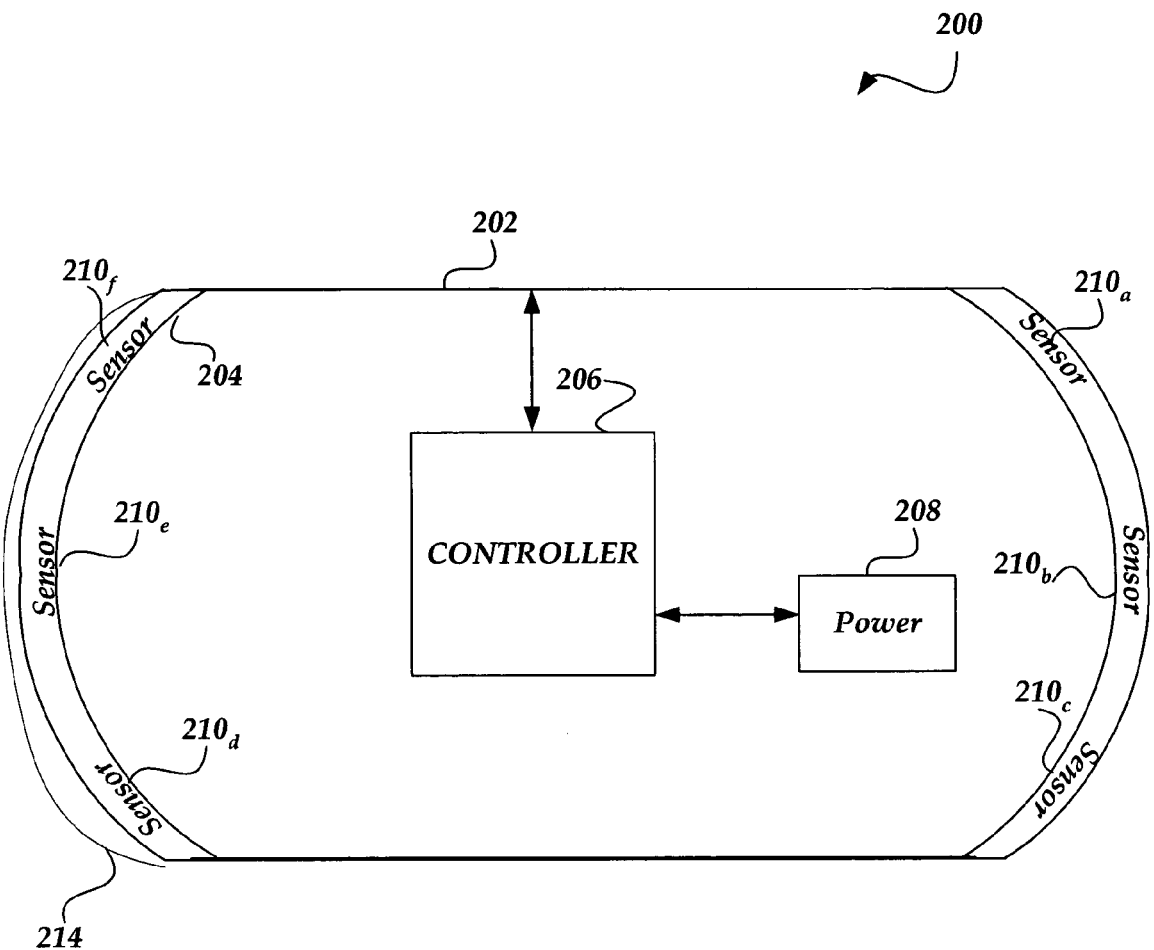
FIG. 2 illustrates a schematic of a capsule endoscope wherein a portion of the shell includes an exemplary sensor configuration.

FIG. 2 illustrates a schematic of a capsule endoscope wherein a portion of the shell includes an exemplary sensor configuration, in accordance with aspects of the present invention. FIG. 2 is similar to FIG. 1 but only a portion of the shell of the CE in FIG. 2 is formed from the curved sensors.

As shown in the figure, CE 200 includes sensors $210_{a-f}$ forming the ends of the CE. Sensors may form any portion of the CE. Alternatively, or in addition, the sensors may be formed to match the contour of the shell 214 of the CE. Additionally, the sensors may include active electronic devices, such as illuminators, transmitters, and the like.

One aspect of the invention includes the fabrication and implementation of a CE shell having a curved surface including sensors. Embodiments of the invention contemplate sensors where the configuration of the curved surface of the sensors substantially matches that of the capsule that the sensor is attached or form. One such embodiment is discussed with respect to FIG. 3B.

Figure 3A:
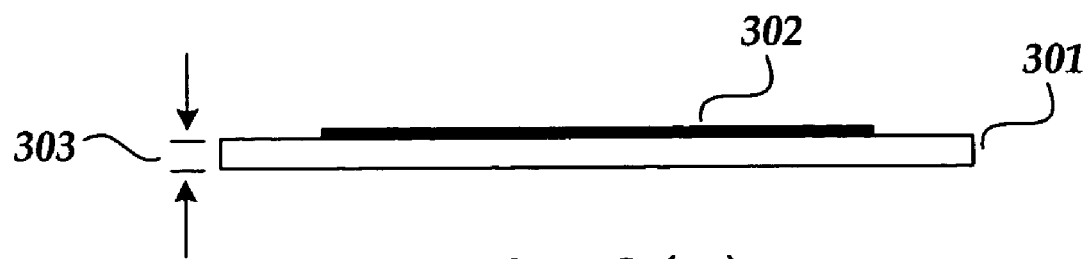
FIGS. 3(a) and 3(b) are cross-section views of a flexible semiconductor substrate and the relationship of such a substrate to a capsule endoscope shell.

FIG. 3A depicts an embodiment of a sensor configuration for a CE constructed in accordance with the principles of the present invention. For purposes of discussion, the exemplary sensor illustrated is an imaging sensor. Other types of sensors (or active electronic devices such as illuminators) may be constructed using the same methodology. Sensor 300 comprises a semiconductor substrate 301 having an array of optical elements 302 formed on its top surface. Suitable semiconductor substrate materials include, but are not limited to, silicon (Si), gallium arsenide (GaAs), gallium indium arsenide (GaInAs). These substrate materials may include other semiconductor materials. The optical elements 302 are formed on the top surface of the substrate 301. Such optical elements commonly include arrays of electronic photo-detector circuitry. The elements can include arrays of photodiodes, charge coupled devices (CCD's), CMOS devices, and numerous other light sensitive optical detectors. The devices can be accompanied or replaced by other optical elements including, but not limited to filters, blockers, and reflectors. Additionally, the principles of the present invention can be applied to other sensors beyond photo imaging devices.

Semiconductor substrate 301 is formed having a substantially reduced thickness 303 when compared to substrates of ordinary thickness. A suitable substrate thickness is on the order of about 25 microns to about 125 microns thick. Such a thin substrate 301 imparts flexibility to substrate 301 while retaining sufficient strength so as to not break when flexed over various angles of curvature. The thinness and flexibility enables substrate 301 to be flexed or bent to obtain a desired surface contour. As such, substrate 301 may be formed to the desired shape of the capsule endoscope shell. The substrate may form the entire CE shell or a portion of the CE shell. Alternatively, the substrate may be contoured to substantially match the contours of the CE shell.

Figure 3B:
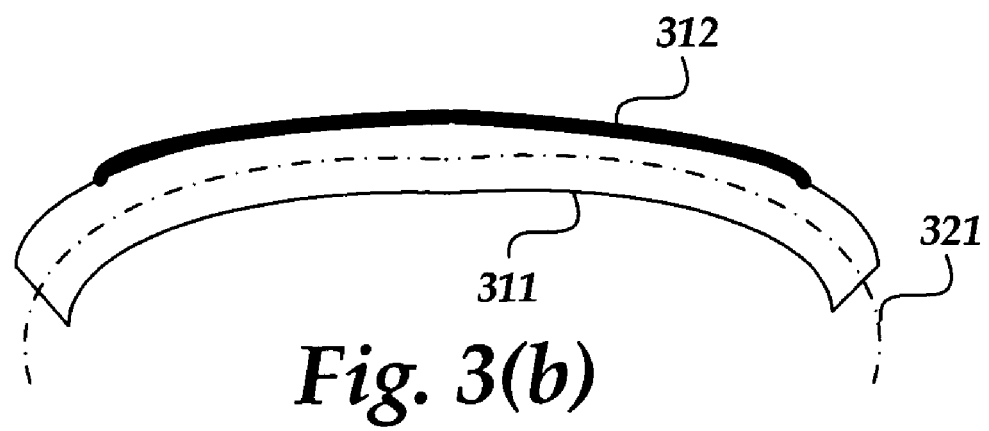

FIG. 3(b) depicts an appropriately thin semiconductor substrate 311 flexed into a curved configuration that substantially conforms to form the shell of a CE. In this way, elements 312 of the sensor may be flexed to match the contour of a CE.

FIGS. 4(a)–4(d) schematically depict an exemplary sensor embodiment and a method embodiment for its fabrication. In the embodiment schematically depicted in FIG. 4(a), a standard semiconductor wafer 401 is shown with a plurality of photo-sensitive detector elements 402 formed on a surface of the wafer. In one example, wafer 401 can be a conventional silicon wafer about 750µ thick, constructed in accordance with ordinary manufacturing processes. According to one embodiment, sensor elements 402 are photoimager arrays. Other optical or electro-optical components, or other sensor elements, can also be formed on the surface. The sensors formed on the surface may be many types of sensors, including sensors for temperature, pH, infrared, and the like. The sensor elements 402 of the depicted embodiment are formed into photoimager arrays in accordance with conventional fabrication techniques.

Figure 4A:
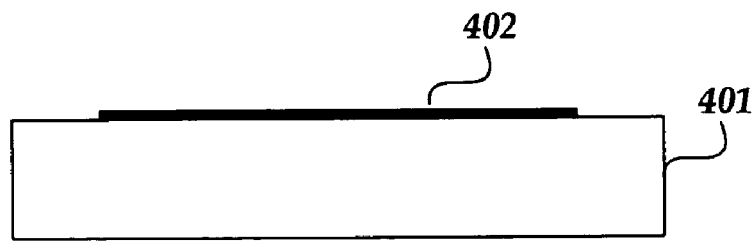
FIGS. 4(a)–4(d) are cross-section views of a portion of a semiconductor substrate showing a process embodiment used for fabricating flexible substrates.
Figure 4B:
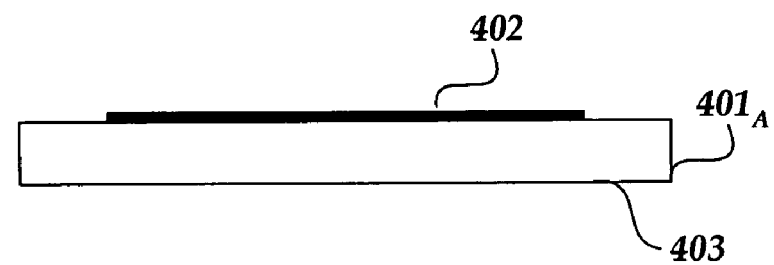
Figure 4C:
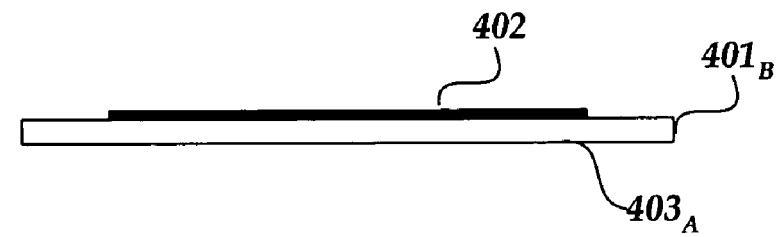

As depicted in FIG. 4(b), the wafer is subjected to a bulk back-grinding process using any one of a number of conventional back-grinding processes. Portions of the backside surface 403 of wafer 401$_A$ are removed to produce the resulting embodiment depicted in FIG. 4(b). In one embodiment, the backside surface is subjected to chemical mechanical polishing (CMP) to remove material from the backside of the wafer. Other methods of bulk material removal can also be used to remove material from the backside of the wafer. Typically, such back-grinding proceeds until the wafer is on the order of about 125 1μ to about 175μ thick. One preferred thickness is on the order of about 150μ thick.

The wafer is then subjected to precision removal of backside material to reach a final desired thickness. In one embodiment depicted in FIG. 4(c), "plasma back-grinding" can be used to remove portions of the backside surface 403$_A$ of wafer 401$_B$. Such precision removal of backside material continues until the wafer 401$_B$ is about 25 to about 100μ thick. The actual thickness is dependent on the wafer material and the degree of flexibility and curvature desired in the final substrate. Some portions of the substrate may be thinner than other portions of the substrate. Many processes can be used to achieve precision removal of material from the backside surface 403$_A$ of the wafer 401$_B$. In one embodiment, atmospheric downstream plasma (ADP) etching is used to thin wafers 401$_B$ by precision removal of backside material. In one example process, a wafer having been subjected to bulk back-grinding is placed in a process chamber of an ADP etch system. For example, a TE-2001 series ADP machine available from Tru-Si Technologies of Sunnyvale, Calif. can be used. An argon flow of about 1 standard liter per minute (slm) is supplied along with a gas flow of suitable fluorine containing gases. Examples of suitable fluorine containing gases include $CF_4$, $SF_6$, as well as other fluorine containing gases. Suitable gas flow rates for the fluorine containing gases are about 4 slm to about 6 slm, but may vary with gas type chosen as well as other process needs. Such precision removal of backside material continues until the wafer 401$_B$ obtains the desired thickness.

One advantage of such precision removal of material (especially; when accomplished using plasma etching techniques) is that stresses induced during bulk back-grinding are relieved by such precision removal of material from the backside surface. Plasma etching does not induce stresses in the wafer. Another advantage of such precision removal of material (especially, with plasma etching) is that it can obtain extremely precise wafer thicknesses for the wafer 401$_B$.

Figure 4D:

In FIG. 4(d), the wafer is shown after singulation into a plurality of separate individual photoimager dies 404. Each die includes an image sensor.

Figure 5A:
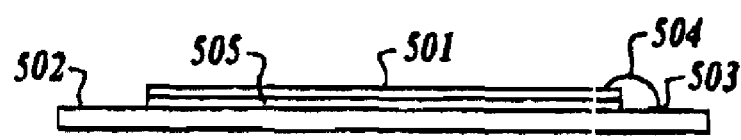
FIG. 5(a) is a cross-section view of a flexible substrate mounted on a flexible support.

Referring to FIG. 5(a) the forgoing embodiment can be further expanded upon. Flexible substrate 501 is coupled with a flexible support 502. Support 502 provides a flexible support that increases the robustness of substrate 501. In one embodiment, support 502 can be formed of a polyimide material. Also, a laminated support 502 can be constructed having alternating layers of copper and polyimide materials. Any material sufficiently flexible can be used as a support 502. An adhesive can be used to couple substrate 501 with flexible support 502. In one example, an epoxy layer 505 about 20μ to about 30μ thick can be used to attach substrate 501 with flexible support 502. Any other approach for coupling substrate 501 with the flexible support 502 may be used. Also, support 502 can provide contact surfaces for electrical connections. In the depicted embodiment, support 502 includes bonding surfaces 503 that can be electrically coupled to the circuitry of substrate 501. For example, bonding surfaces 503 can be wire-bonded to substrate 501 using connector wires 504.

Figure 5B:
FIG. 5(b) is a cross-section view of an embodiment of a sensor module employing a flexible substrate mounted on a flexible support.

FIG. 5(b) depicts a portion of one embodiment of a CE incorporating a sensor module 510 as part of its shell. In one embodiment, sensor module 510 may include each of the components illustrated in FIG. 5(a). For example, using support 502 and substrate 501 of FIG. 5(a), the electrical connections are encapsulated by protective layer 506 (e.g., a moisture resistant epoxy), a portion of which is illustrated in FIG. 5(b). Support 502 and substrate 501 are curved into a contour that matches the desired surface of a CE shell.

Figure 5C:
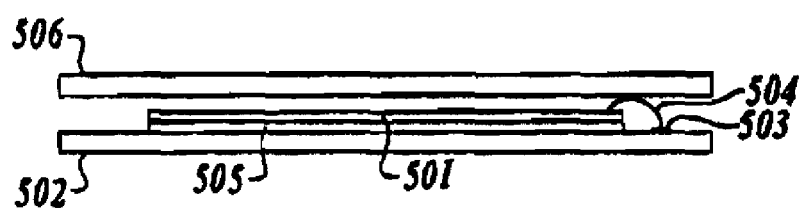
FIG. 5(c) is a cross-section view of a portion of a flexible substrate mounted on a flexible support showing a portion of a protective layer encapsulating the electrical connection.

FIG. 5(c) illustrates a portion of the sensor for one embodiment, which a portion of substrate 501 coupled with support 502, and protective layer 506, where the electrical connections are encapsulated by protective layer 506.

Figure 6:
FIG. 6 is a view of a rigid support having a preformed mounting surface with a curved mounting surface.

FIG. 6 shows a view of a rigid support having a preformed mounting surface with a curved mounting surface, in accordance with aspects of the present invention. This embodiment makes use of a rigid support structure (602) having a curved surface portion of the rigid support, and substrate 601. Embodiments can assume a number of different shapes. Such rigid supports can be formed of a multitude of different materials including, but not limited to ceramics and plastics.

Figure 7:
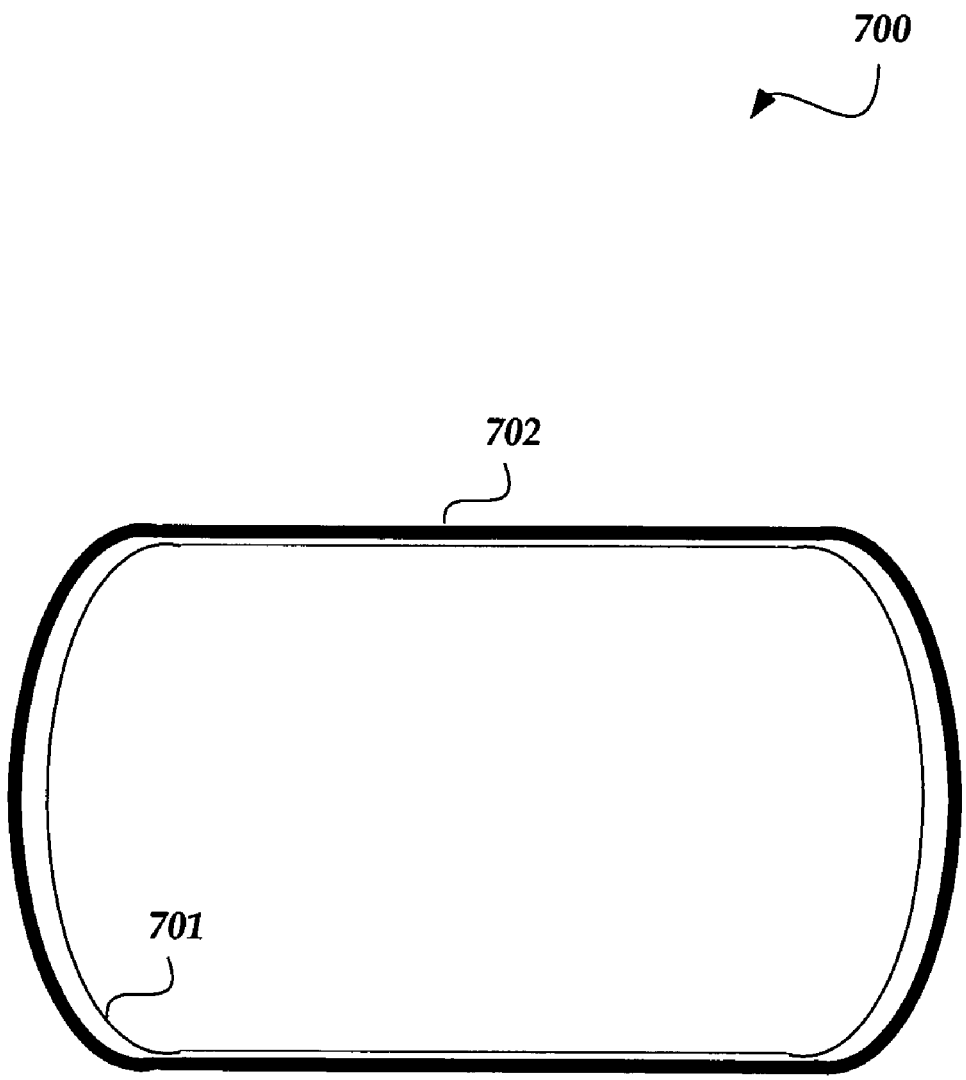
FIG. 7 is an exemplary CE shell formed by a flexible substrate; in accordance with aspects of the present invention.

FIG. 7 is an exemplary CE shell formed by a flexible substrate, in accordance with aspects of the present invention. Sensor circuitry 702 (e.g., a photo detector array, temperature sensors, and the like) is formed on a surface of substrate 701. The substrate 701 (with sensor circuitry 702) may be coupled with a rigid support or a flexible support. The surface contour of the curved surface portion is configured so that substrate 701 may be fitted onto the curved surface portion of CE 700, or form the shell of CE 700. In the depicted implementation, substrate 701 is coupled with a support using an adhesive. For example, an epoxy layer about 20μ to about 30μ thick can be used to attach the substrate 701 with the support. Other coupling approaches may be used to couple substrate 701.

The support and substrate 701 may be mounted inside a protective housing (not shown). The housing may include an optically transmissive surface (or window) through which light can pass onto sensor circuitry 702. The optically transmissive surface may be configured to allow visible wavelengths as well as non-visible wavelengths to pass onto sensor circuitry 702. A lens (not shown) can be mounted above the sensor circuitry at a desired optical distance from sensor circuitry 702 thereby optically coupling the lens with the sensor circuitry 702 and completing an optical imaging module.

According to another embodiment of the invention, the sensor circuitry may be formed using organic semiconductors. Organic semiconductors are low-cost semiconductors that may be formed as a thin film on almost any substrate. The substrate may be flexible or rigid. The organic semiconductor may be applied over any substrate used for the shell. The substrate may include a metal substrate, a plastic substrate, a ceramic substrate, and the like.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An apparatus, comprising:
   a capsule endoscope having a shape, wherein the shape has a contour, at least a portion of the contour is curved, and wherein the capsule endoscope includes:
   a shell, wherein the shell includes one or more sensors, and wherein at least one of the one or more sensors is curved to shape to the contour, wherein the capsule endoscope further includes a substrate that includes the one or more sensors, wherein the substrate is formed sufficiently thin that it can be shaped to the contour, and wherein the capsule endoscope further includes:

a support having sufficient flexibility such that the support can be formed to the contour, wherein the substrate is coupled with the support such that the combination can be formed to the contour.

2. The apparatus of claim 1, wherein the support is formed of a laminate of polyimide and copper layers; and wherein the substrate is comprised of a semiconductor substrate.

3. The apparatus of claim 1, wherein the capsule endoscope further includes a protective housing, and wherein the support and substrate are arranged inside of the protective housing.

4. The apparatus of claim 3, wherein the protective housing includes a portion of an optically transmissive surface.

5. A device, comprising:

a capsule endoscope having a shape, wherein the shape has a contour, at least a portion of the contour is curved, and wherein the capsule endoscope includes:

one or more sensors, and wherein at least one of the one or more sensors includes a semiconductor material that is curved to shape to the contour, wherein the capsule endoscope further includes a support having sufficient flexibility such that the support can be formed to the contour, the substrate is coupled with the support such that the combination can be formed to the contour, the support has electrical contact pads formed thereon; wherein the one or more sensors of the substrate have electrical contacts; the electrical contacts of the substrate are electrically connected to the electrical contact pads of the support; and wherein electrical connections between the electrical contact pads of the support and the electrical contacts of the sensors of the substrate are encapsulated with a protective covering.

6. The device of claim 5, wherein a sensor of the one or more sensors is at least one of: a temperature sensor, a pH sensor, an infrared sensor, an imaging sensor, or an active sensor.

7. The device of claim 5, wherein the capsule endoscope further includes a lens covering at least one of the one or more sensors.

8. The device of claim 5, wherein the one or more sensors are made of an organic semiconductor.

9. The device of claim 5, wherein the capsule endoscope includes a shell that is curved to the shape of the contour.

10. The device of claim 9, wherein the shell is distinct from the one or more sensors.

11. The device of claim 9, wherein the one or more sensors form a portion of the shell.

12. The device of claim 9, wherein the capsule endoscope further includes an outer shell that covers at least a portion of the shell.

13. The device of claim 9, wherein the capsule endoscope further includes a covering that is applied over at least a portion of the shell.

14. The device of claim 5, wherein the semiconductor material is formed sufficiently thin that it can be shaped to the contour.

15. The device of claim 14, wherein the substrate includes a silicon material.

16. The device of claim 14, wherein the substrate has a thickness of about 25 microns to about 125 microns.

17. The device of claim 14, further comprising an illuminator positioned on the shell.

18. The device of claim 5, wherein the support is formed of a laminate of polyimide and copper layers; and wherein the substrate is comprised of a semiconductor substrate.

19. The device of claim 5, wherein the capsule endoscope further includes a protective housing, and wherein the support and substrate are arranged inside of the protective housing.

20. The device of claim 19, wherein the protective housing includes a portion of an optically transmissive surface.

* * * * *